United States Patent [19]

Rusch

[11] Patent Number: 5,451,562
[45] Date of Patent: Sep. 19, 1995

[54] PHOSPHONATE/PHOSPHINATE CONTAINING HERIBICDAL COMPOSITIONS AND THE USE THEREOF

[75] Inventor: Reinhart Rusch, Berlin, Germany

[73] Assignee: Schering Aktiengesellschaft, Germany

[21] Appl. No.: 199,267

[22] PCT Filed: Aug. 27, 1992

[86] PCT No.: PCT/EP92/01973

§ 371 Date: Feb. 28, 1994

§ 102(e) Date: Feb. 28, 1994

[87] PCT Pub. No.: WO93/04585

PCT Pub. Date: Mar. 18, 1993

[30] Foreign Application Priority Data

Aug. 30, 1991 [DE] Germany .......... 91 18 565.2

[51] Int. Cl.$^6$ ............ A01N 57/04
[52] U.S. Cl. ............ 504/127; 504/128; 504/133; 504/136; 504/137; 504/140; 504/143
[58] Field of Search ............ 504/127, 128, 133, 136, 504/137, 140, 143

[56] References Cited

U.S. PATENT DOCUMENTS 2,927,014  3/1960  Goyette .............. 504/207

*Primary Examiner*—Richard L. Raymond
*Assistant Examiner*—B. Bembenick
*Attorney, Agent, or Firm*—Ostrolenk, Faber, Gerb & Soffen

[57] ABSTRACT

A herbicidal composition which comprises a phosphonate or phosphinate of the formula $$(RO)_x \overset{O}{\underset{\|}{P}}(R')_y$$

where R and R$^1$, which may be the same or different, each represent straight or branch-chained alkyl of 1 to 12 carbon atoms, and x and y are each 1 or 2, the sum of x an y being 3; and phenmedipham, desmedipham, metamitron, lenacil, ethofumesate or chloridazon in association with a suitable carrier and/or surface active agent, and a method of combating weeds.

11 Claims, No Drawings

PHOSPHONATE/PHOSPHINATE CONTAINING HERIBICDAL COMPOSITIONS AND THE USE THEREOF

This invention concerns new herbicidal compositions and methods of combating weeds.

PRIOR ART

U.S. Pat. No 2927014 discloses phosphonates and phosphinates having herbicidal activity. We have now found that combinations of certain alkyl substituted phosphonates and phosphinates according to the U.S. Patent with certain known sugar beet herbicides are surprisingly beneficial and synergistic.

DESCRIPTION

In one aspect, the invention provides a herbicidal composition comprising:

(a) at least one phosphonate or phosphinate of the formula:

$$(RO)_x P(R')_y \quad (I)$$

where R and $R^1$, which may be the same or different, each represent straight or branch-chained alkyl of 1 to 12 carbon atoms, and x and y are each 1 or 2, the sum of x and y being 3; and (b) at least one compound selected from phenmedipham, desmedipham, metamitron, lenacil, ethofumesate and chloridazon, or a combination of 2 and more in association with a suitable carrier and/or surface active agent.

In another aspect, the invention provides a method of combating weeds which comprises applying to a locus infested or liable to be infested therewith, an effective amount of the two components (a) and (b).

Preferred compounds of formula I are those wherein R and $R^l$ each represent 2-ethylhexyl or dodecyl, especially 0,0-bis(2-ethylhexyl) (2-ethylhexyl) phosphonate.

The ratio by weight of (a) to (b) employed is preferably from 10:1 to 1:10, especially from 5:1 to 1:5.

The compositions of the invention are herbicidally-active against a wide range of broad-leaved and grass weeds, including Alopecurus, Echinochloa, Setaria, Amaranthus, Atriplex, Centaurea, Galium, Matricaria, Mercurialis, Polygonum and Stellaria species, but are comparatively safe to certain crop species, particularly beets. They may thus be of use as herbicides, and especially as selective herbicides, particularly in the control of a range of weeds in such crops.

The compositions of the invention usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic Solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxy ethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulphonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulphates such as sodium dodecyl sulphate, ethoxylated fatty alcohol sulphates, ethoxylated alkylphenol sulphates, lignin sulphates, petroleum sulphonates, alkylaryl sulphonates such as alkyl-benzene sulphonates or lower alkylnaphthalene sulphonates, salts of sulphonated naphthaleneformaldehyde condensates, salts of sulphonated phenolformaldehyde condensates, or more complex sulphonates such as the amide sulphonates, e.g. the sulphonated condensation product of oleic acid and N-methyl taurine or the dialkyl sulfosuccinates e.g. the sodium sulphonate of dioctyl succinate.

The surface active agents may also comprise non-ionic agents, for example condensation products or fatty acid esters, fatty alcohols, fatty acid amides or alkyl-substitutedphenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyn-4,7-diol, or ethoxylated acetylenic glycols. The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulphates, lignin sulphonates, alkyl-aryl sulphonates, salts of sulphonated naphthaleneformaldehyde condensates, salts of sulphonated phenolformaldehyde condensates, sodium oleoyl N-methyltauride, dialkyl sulfosuccinates, alkyl phenol ethoxylates, and fatty alkyl ethoxylates.

If the components (a) and (b) are applied sequentially, they may each be applied in a composition analogous to those described above.

If desired, the compositions may contain one or more further active ingredients, eg herbicides, fungicides or insecticides in addition to components (a) and (b).

The present compound may be applied to plants, the soil, land or aquatic areas, and particularly to a locus at which a crop is growing. The method is particularly active post-emergence.

In the present method, the amount of (a) applied is preferably from 0.01 to 1 kg/ha, preferably from 0.05 to 0.25 kg/ha. The amount of (b) applied is preferably from 0.01 to 2 kg/ha, preferably from 0.05 to 0.5 kg/ha. The amount of (a) and (b) in total applied is preferably from 0.3 to 3 kg/ha.

EXAMPLE

The invention is illustrated by the following Examples in which the compounds employed are identified as follows:

I O,O-bis (2-ethylhexyl) (2-ethylhexyl)phosphonate
II phenmedipham
III metamitron
IV lenacil
V chloridazon
V desmedipham and plant species are identified as follows:
a *Alopecurus myosuroides*
b *Amaranthus retroflexus*
c *Atriplex hortensis*
d *Beta vulgaris altissima*
e *Beta vulgaris crassa*
f *Beta vulgaris conditiva*
g *Centaurea cyanus*
h *Echinochloa crus-galli*
i *Galium aparine*
j *Matricaria chamomilla*
k *Mercurialis annua*
l *Setaria italica*
m *Stellaria media.*

All rates of application are given as grams active ingredient per hectare (g a.i./ha).

Example 1

The compounds listed below were applied alone and in combination at the rates indicated to beets and weed seedlings grown in a greenhouse. Herbicidal effects were noted 6–10 days after application on a scale of from 0 (no effect) to 10 (complete kill).

| Compds | Rate | a | i | j | k | d | f |
|---|---|---|---|---|---|---|---|
| I | 300 | 0.5 | 0.5 | 0.0 | 0.2 | 0.5 | 1.0 |
|  | 1000 | 1.0 | 2.0 | 0.5 | 0.5 | 2.2 | 3.5 |
| I + II | 250 + 50 | 3.0 | 4.5 | 1.5 | 2.5 | 0.8 | 0.5 |
|  | 200 + 100 | 4.5 | 7.0 | 4.0 | 1.5 | 0.8 | 0.5 |
|  | 150 + 150 | 4.5 | 6.5 | 4.5 | 1.0 | 0.8 | 0.0 |
|  | 100 + 200 | 4.0 | 6.5 | 4.5 | 2.0 | 1.0 | 0.0 |
|  | 50 + 250 | 3.5 | 4.5 | 4.5 | 2.0 | 0.8 | 0.0 |
| II | 300 | 3.5 | 5.0 | 3.5 | 0.5 | 0.5 | 0.5 |
|  | 1000 | 5.0 | 8.0 | 6.0 | 2.5 | 0.5 | 2.0 |

| Compds | Rate | a | b | c | g | i | j | m | d |
|---|---|---|---|---|---|---|---|---|---|
| I | 300 | 0.5 | 3.0 | 1.0 | 1.0 | 0.5 | 0.0 | 1.0 | 0.5 |
|  | 1000 | 1.0 | 3.5 | 2.5 | 1.5 | 2.0 | 0.5 | 1.5 | 2.2 |
| I + III | 250 + 50 | 1.0 | 3.0 | 3.0 | 2.0 | 2.0 | 3.5 | 2.0 | 1.2 |
|  | 200 + 100 | 1.0 | 4.5 | 3.5 | 2.0 | 3.0 | 4.5 | 2.0 | 0.5 |
|  | 150 + 150 | 2.0 | 4.5 | 4.5 | 1.5 | 4.0 | 5.0 | 2.0 | 0.8 |
|  | 100 + 200 | 2.0 | 5.0 | 4.0 | 1.5 | 2.5 | 4.0 | 2.0 | 0.5 |
|  | 50 + 250 | 1.5 | 4.0 | 3.0 | 1.0 | 2.0 | 3.0 | 2.5 | 0.4 |
| III | 300 | 0.5 | 2.5 | 0.5 | 1.5 | 0.5 | 3.0 | 0.0 | 0.2 |
|  | 1000 | 4.0 | 3.5 | 2.5 | 2.5 | 1.5 | 6.0 | 0.5 | 0.2 |

Example 2

The compounds listed below were applied alone and in combination at the rates indicated to beets and weed seedlings grown in a greenhouse. The plants were harvested 8 to 14 days after treatment, and the harvested weights were measured. The percentage weight reductions relative to an untreated control were as follows:

| Compds | Rate | a | g | i | k | d | e | f |
|---|---|---|---|---|---|---|---|---|
| I | 300 | 5 | 0 | 32 | 8 | 5 | 2 | 0 |
|  | 1000 | 12 | 4 | 42 | 0 | 12 | 5 | 0 |
| I + II | 250 + 50 | 37 | 19 | 80 | 7 | 2 | 3 | 2 |
|  | 200 + 100 | 59 | 22 | 86 | 25 | 1 | 8 | 0 |
|  | 150 + 150 | 59 | 28 | 87 | 7 | 5 | 8 | 0 |
|  | 100 + 200 | 55 | 25 | 85 | 26 | 4 | 10 | 0 |
|  | 50 + 250 | 57 | 22 | 85 | 48 | 0 | 6 | 1 |
| II | 300 | 52 | 23 | 79 | 16 | 0 | 3 | 0 |
|  | 1000 | 67 | 39 | 92 | 29 | 4 | 24 | 16 |

| Compds | Rate | b | c | g | i | m | d | e | f |
|---|---|---|---|---|---|---|---|---|---|
| I | 300 | 12 | 2 | 0 | 32 | 4 | 5 | 2 | 0 |
|  | 1000 | 23 | 39 | 4 | 42 | 14 | 12 | 5 | 0 |
| I + III | 250 + 50 | 27 | 53 | 10 | 55 | 36 | 4 | 4 | 0 |
|  | 200 + 100 | 41 | 62 | 15 | 69 | 50 | 0 | 7 | 0 |
|  | 150 + 150 | 46 | 73 | 19 | 70 | 54 | 0 | 0 | 6 |
|  | 100 + 200 | 50 | 69 | 19 | 69 | 54 | 0 | 2 | 0 |
|  | 50 + 250 | 47 | 53 | 17 | 61 | 46 | 0 | 1 | 0 |
| III | 300 | 18 | 6 | 7 | 45 | 24 | 0 | 3 | 0 |
|  | 1000 | 51 | 55 | 23 | 70 | 53 | 0 | 0 | 0 |
| Control |  | 0 | 0 | 0 | 0 | 0 | 0 | 0 | 0 |

| Compds | Rate | c | h | i | l | m | d | f |
|---|---|---|---|---|---|---|---|---|
| I | 300 | 2 | 0 | 32 | 23 | 4 | 5 | 0 |
|  | 1000 | 39 | 20 | 42 | 46 | 14 | 12 | 0 |
| I + IV | 250 + 50 | 4 | 21 | 36 | 27 | 1 | 0 | 0 |
|  | 200 + 100 | 12 | 25 | 45 | 41 | 14 | 3 | 0 |
|  | 150 + 150 | 37 | 28 | 54 | 41 | 16 | 12 | 4 |
|  | 100 + 200 | 57 | 27 | 58 | 46 | 17 | 13 | 4 |
|  | 50 + 250 | 40 | 26 | 50 | 41 | 26 | 4 | 5 |
| IV | 300 | 0 | 16 | 17 | 25 | 3 | 0 | 0 |
|  | 1000 | 15 | 32 | 34 | 33 | 13 | 0 | 0 |
| Control |  | 0 | 0 | 0 | 0 | 0 | 0 | 0 |

| Compds | Rate | b | c | g | h | i | l | m | f |
|---|---|---|---|---|---|---|---|---|---|
| I | 600 | 15 | 20 | 4 | 12 | 15 | 26 | 8 | 0 |
|  | 2000 | 30 | 70 | 25 | 57 | 14 | 32 | 33 | 5 |
| I + V | 500 + 100 | 57 | 81 | 17 | 48 | 69 | 54 | 40 | 6 |
|  | 400 + 200 | 74 | 83 | 16 | 49 | 74 | 55 | 43 | 11 |
|  | 300 + 300 | 65 | 82 | 17 | 57 | 76 | 56 | 50 | 7 |
|  | 200 + 400 | 68 | 83 | 18 | 52 | 74 | 47 | 41 | 9 |
|  | 100 + 500 | 46 | 77 | 17 | 50 | 64 | 41 | 35 | 2 |
| V | 600 | 18 | 22 | 3 | 35 | 30 | 23 | 15 | 0 |
|  | 2000 | 42 | 49 | 22 | 59 | 45 | 41 | 39 | 2 |
| Control |  | 0 | 0 | 0 | 0 | 0 | 0 | 0 | 0 |

| Compds | Rate | a | c | g | i | j | m | f |
|---|---|---|---|---|---|---|---|---|
| I | 500 | 10 | 0 | 0 | 0 | 13 | 6 | 7 |
|  | 1000 | 31 | 50 | 8 | 0 | 20 | 56 | 27 |
| I + VI | 300 + 200 | 50 | 73 | 46 | 62 | 59 | 78 | 0 |
|  | 600 + 400 | 66 | 86 | 67 | 81 | 76 | 89 | 30 |
| VI | 500 | 28 | 36 | 45 | 51 | 60 | 65 | 2 |
|  | 1000 | 55 | 73 | 58 | 75 | 68 | 84 | 32 |
| Control |  | 0 | 0 | 0 | 0 | 0 | 0 | 0 |

| Compds | Rate | a | c | g | j | h | i | e |
|---|---|---|---|---|---|---|---|---|
| I | 680 | 14 | 31 | 0 | 13 | 19 | 0 | 27 |
| I + II | 680 + 450 | 55 | 71 | 57 | 79 | 71 | 90 | 13 |
| II | 450 | 18 | 1 | 16 | 48 | 18 | 40 | 0 |

| -continued | | | | | | | | |
|---|---|---|---|---|---|---|---|---|
| Control | 0 | 0 | 0 | 0 | 0 | 0 | 0 | |
| Compds | Rate | | a | h | i | j | m | d |
| I | 300 | | 0 | 0 | 0 | 0 | 4 | 5 |
| | 1000 | | 19 | 27 | 17 | 6 | 8 | 10 |
| I + II + VI | 193 + 53.5 + 53.5 | | 35 | 85 | 79 | 50 | 33 | 0 |
| | 430 + 120 + 120 | | 46 | 86 | 90 | 70 | 43 | 9 |
| II + VI | 150 + 150 | | 18 | 72 | 54 | 32 | 18 | 0 |
| | 335 + 335 | | 41 | 79 | 80 | 53 | 28 | 2 |
| Control | | | 0 | 0 | 0 | 0 | 0 | 0 |

Example 3:

The compounds listed below were applied alone and in combination at the rates indicated to beets and weed seedlings grown in a greenhouse. Herbicidal effects were noted 6–10 days after application on a scale from 0 (no effect) to 10 (complete kill). Results were obtained as follows:

| a) | with compound VII | g a.i./ha | m |
|---|---|---|---|
| | ethofumesate VII | 600 | 4.0 |
| | VII<br>+<br>diethylmethylphosphonate<br>(ZK 146 953) (VIII) | 500<br>+<br>100 | 5.0 |
| | VII + VIII | 400<br>+<br>200 | 4.5 |
| | VIII | 600 | 0.1 |
| | VII<br>+<br>diethylethylphosphonate<br>(ZK 53 491) (IX) | 500<br>+<br>100 | 4.5 |
| | VII + IX | 400<br>+<br>200 | 4.5 |
| | IX | 600 | 0.2 |
| b) | with compound II | g a.i./ha | j |
| | II | 300 | 3.5 |
| | II +<br>dipentylpentylphosphonate<br>(ZK 148 236) (X) | 100 + 200<br>150 + 150 | 6.5<br>4.0 |
| | X | 300 | 0 |
| | II +<br>dibutylbutylphosphonate<br>(ZK 147 326) (XI) | 200 + 100<br>100 + 200 | 5<br>5.5 |
| | (XI) | 300 | 0.5 |
| | II +<br>diisopropylallylphosphonate<br>(ZK 147 327) (XII) | 200 + 100<br>100 + 200 | 5<br>5.5 |
| | XII | 300 | 0 |
| | II +<br>diisoproyplmethylphosphonate<br>(ZK 146 952) (XIII) | 200 + 100<br>100 + 200 | 4.0<br>4.5 |
| | XIII | 300 | 0 |

I claim:
1. A herbicidal composition comprising a synergistic combination of:
 (a) at least one phosphonate or phosphinate of the formula:

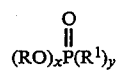

where R and R', which may be the same or different, each represent straight or branch-chained alkyl of 1 to 12 carbon atoms, and x and y are each 1 or 2, the sum of x and y being 3; and
 (b) at least one compound selected from phenmedipham, desmedipham, metamitron, lenacil, ethofumesate and chloridazon, the ratio by weight of component (a) to component (b) being from 1:10 to 10:1;
 in association with a suitable carrier and/or surface active agent.

2. A composition according to claim 1 in which each R and $R^1$ group in the compound of formula I is 2-ethylhexyl or dodecyl.

3. A composition according to claim 1 in which x in the compound of formula I is 2.

4. A composition according to claim 1 in which the ratio by weight of component (a) to component (b) is from 1:5 to 5:1.

5. A method of combating weeds which comprises applying to a locus infested or liable to be infested therewith, and effective amount of the two components (a) and (b) as defined in claim 1 the ratio by weight of component (a) to component (b) being from 1:10 to 10:1, and in which the amount of (a) applied is 0.01 to 1 kg/ha.

6. A method according to claim 5 in which the amount of component (a) applied is from 0.05 to 0.25 kg/ha.

7. A method according to claim 5 in which the amount of (b) applied is from 0.01 to 2 kg/ha.

8. A method according to claim 5 in which the total amount of components (a) and (b) applied is from 0.03 to 3 kg/ha.

9. A method according to claim 5 in which each R and R' group in the compound of formula I is 2-ethylhexyl or dodecyl.

10. A method according to claim 9 in which compound I is a O, O-bis(2-ethylhexyl) (2-ethylhexyl) phosphonate.

11. A composition according to claim 2 in which the compound of formula I is O,O-bis(2-ethylhexyl) (2-ethylhexyl) phosphonate.

* * * * *